(12) United States Patent
Hutton et al.

(10) Patent No.: US 9,308,398 B2
(45) Date of Patent: Apr. 12, 2016

(54) MULTIPLE PRODUCT SYSTEM FOR HAIR COMPRISING A CONDITIONER WITH A SPECIFIC YIELD POINT

(75) Inventors: Howard David Hutton, Oregonia, OH (US); Toshiyuki Okada, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 674 days.

(21) Appl. No.: 12/794,240

(22) Filed: Jun. 4, 2010

(65) Prior Publication Data

US 2011/0048449 A1    Mar. 3, 2011

Related U.S. Application Data

(60) Provisional application No. 61/184,053, filed on Jun. 4, 2009.

(51) Int. Cl.
| | |
|---|---|
| *C11D 1/62* | (2006.01) |
| *C11D 1/29* | (2006.01) |
| *C11D 1/37* | (2006.01) |
| *C11D 1/65* | (2006.01) |
| *C11D 1/82* | (2006.01) |
| *C11D 9/36* | (2006.01) |
| *A61Q 5/12* | (2006.01) |
| *A61K 8/34* | (2006.01) |
| *A61K 8/41* | (2006.01) |
| *A61K 8/46* | (2006.01) |
| *A61Q 5/02* | (2006.01) |

(52) U.S. Cl.
CPC . *A61Q 5/12* (2013.01); *A61K 8/342* (2013.01); *A61K 8/416* (2013.01); *A61K 8/46* (2013.01); *A61Q 5/02* (2013.01); *A61K 2800/884* (2013.01)

(58) Field of Classification Search
CPC .............. C11D 1/62; C11D 1/29; C11D 1/37; C11D 3/0094; C11D 3/162; C11D 1/65; C11D 1/82; C11D 3/2013; C11D 3/373; C11D 9/36

See application file for complete search history.

(56) References Cited

U.S. PATENT DOCUMENTS

| | | | |
|---|---|---|---|
| 3,249,550 A | 5/1966 | Metters | |
| 3,616,859 A | 11/1971 | Shay et al. | |
| 4,024,078 A | 5/1977 | Gilbert et al. | |
| 4,294,728 A | 10/1981 | Vanlerberghe et al. | |
| 4,753,754 A | 6/1988 | Messenger | |
| 4,980,078 A | 12/1990 | Verite et al. | |
| 5,077,042 A | 12/1991 | Darkwa | |
| 5,106,613 A * | 4/1992 | Hartnett et al. | 424/70.122 |
| RE34,584 E | 4/1994 | Grote | |
| 5,415,857 A * | 5/1995 | Robbins et al. | 424/70.122 |
| 5,440,032 A | 8/1995 | Hirosawa et al. | |
| 5,482,543 A | 1/1996 | Bleve et al. | |
| 5,580,850 A | 12/1996 | Bigorra | |
| 5,610,127 A | 3/1997 | Erilli et al. | |
| 5,635,466 A | 6/1997 | Burdon et al. | |
| 5,695,748 A | 12/1997 | Francis | |
| 5,741,948 A | 4/1998 | Kirishiki et al. | |
| 5,750,099 A | 5/1998 | Yoshihara | |
| 5,814,323 A | 9/1998 | Lyle | |
| 5,906,972 A | 5/1999 | Gabriel et al. | |
| 5,942,485 A | 8/1999 | Kemen | |
| 5,958,868 A | 9/1999 | Pi Subirana et al. | |
| 5,994,595 A | 11/1999 | Onda et al. | |
| 6,074,633 A | 6/2000 | Dubief et al. | |
| 6,150,322 A | 11/2000 | Singleton et al. | |
| 6,207,629 B1 | 3/2001 | Gonzalez et al. | |
| 6,399,045 B1 | 6/2002 | Morgan et al. | |
| 6,417,408 B2 | 7/2002 | Onda et al. | |
| 6,432,420 B2 | 8/2002 | Ellis et al. | |
| 6,471,953 B1 | 10/2002 | N'Guyen | |
| 6,645,480 B2 | 11/2003 | Giles | |
| 6,706,931 B2 | 3/2004 | Edwards | |
| 6,849,252 B1 | 2/2005 | Yang | |
| 6,884,275 B2 | 4/2005 | Okada et al. | |
| 6,946,437 B2 | 9/2005 | Aizawa et al. | |
| 7,169,745 B2 * | 1/2007 | Kasturi et al. | 510/433 |
| 7,208,480 B2 | 4/2007 | Williams et al. | |
| 7,666,825 B2 | 2/2010 | Wagner et al. | |
| 2002/0041854 A1 | 4/2002 | Hadasch et al. | |
| 2002/0122772 A1 | 9/2002 | Lukenbach et al. | |
| 2002/0151738 A1 | 10/2002 | Edwards | |
| 2003/0083210 A1 | 5/2003 | Goldberg et al. | |
| 2003/0130145 A1 * | 7/2003 | Patel et al. | 510/119 |
| 2004/0092413 A1 | 5/2004 | Ticktin | |
| 2004/0116539 A1 | 6/2004 | Biercevicz | |
| 2004/0166071 A1 | 8/2004 | Pfaffernoschke et al. | |
| 2004/0166074 A1 | 8/2004 | Darkwa | |
| 2004/0235689 A1 | 11/2004 | Sakai et al. | |
| 2004/0254253 A1 | 12/2004 | Culeron | |

(Continued)

FOREIGN PATENT DOCUMENTS

| | | |
|---|---|---|
| DE | 19534372 A1 | 9/1995 |
| EP | 336803 B1 | 9/1992 |
| EP | 0573329 B1 | 7/1997 |
| EP | 0834307 A2 | 4/1998 |
| EP | 1009787 B1 | 6/2000 |
| EP | 1696023 B1 | 4/2008 |
| EP | 1572333 B1 | 5/2008 |
| JP | 56001895 A | 1/1981 |
| JP | 58006209 A | 1/1983 |
| JP | 63143935 A2 | 6/1988 |
| JP | 6107888 A | 4/1994 |
| JP | 07034089 A | 2/1995 |
| JP | 09249900 A | 9/1997 |
| JP | 2002038200 | 2/2002 |
| JP | 2003205039 A2 | 7/2003 |
| JP | 2005113067 A | 4/2005 |
| JP | 2005232118 | 9/2005 |
| JP | 2005255627 A2 | 9/2005 |

(Continued)

OTHER PUBLICATIONS

Bran Luebbe, "Continuous Dilution of Concentrated Alkyl Ether Sulfates", vol. 103—No. 16/1977, 465-466.
XP002545441, Thomson, 1 page.
XP002545442, Thomson, 1 page.

*Primary Examiner* — Charles Boyer
(74) *Attorney, Agent, or Firm* — Carl J. Roof; Angela K. Haughey

(57) ABSTRACT

A multiple product system regimen for providing improved conditioning benefits to hair.

11 Claims, No Drawings

(56) References Cited

U.S. PATENT DOCUMENTS

| | | |
|---|---|---|
| 2004/0266652 A1 | 12/2004 | Brown et al. |
| 2004/0266656 A1 | 12/2004 | Sakurai |
| 2005/0063934 A1 | 3/2005 | Baker |
| 2005/0166338 A1 | 8/2005 | Arango |
| 2005/0192196 A1 | 9/2005 | Hutton |
| 2005/0241076 A1 | 11/2005 | Bureiko |
| 2006/0024256 A1 | 2/2006 | Wells |
| 2006/0035807 A1* | 2/2006 | Kasturi et al. ............ 510/475 |
| 2006/0078528 A1 | 4/2006 | Yang et al. |
| 2006/0078529 A1 | 4/2006 | Uchida |
| 2006/0083703 A1 | 4/2006 | Torgerson |
| 2006/0083704 A1 | 4/2006 | Torgerson |
| 2006/0128596 A1 | 6/2006 | Koshti et al. |
| 2006/0251605 A1 | 11/2006 | Belmar et al. |
| 2006/0286060 A1 | 12/2006 | Yang |
| 2007/0014823 A1 | 1/2007 | Iwata |
| 2007/0041929 A1 | 2/2007 | Torgerson |
| 2007/0119864 A1 | 5/2007 | Tsai |
| 2007/0215642 A1 | 9/2007 | Van der Heijden |
| 2007/0286837 A1 | 12/2007 | Torgerson |
| 2008/0139434 A1 | 6/2008 | Basappa et al. |
| 2008/0153730 A1 | 6/2008 | Tsaur et al. |
| 2009/0123408 A1* | 5/2009 | Kimura et al. ............ 424/70.22 |
| 2009/0155383 A1* | 6/2009 | Kitko et al. ............... 424/642 |
| 2009/0221463 A1* | 9/2009 | Kitko et al. ............... 510/120 |
| 2009/0227482 A1 | 9/2009 | Dong et al. |
| 2009/0246236 A1* | 10/2009 | Kitko et al. ............... 424/401 |
| 2009/0274642 A1* | 11/2009 | Dawson et al. ............ 424/74 |
| 2009/0291058 A1* | 11/2009 | Woodland et al. ........ 424/70.28 |
| 2009/0324527 A1 | 12/2009 | Okada |
| 2009/0324528 A1 | 12/2009 | Okada |
| 2009/0324529 A1 | 12/2009 | Okada |
| 2009/0324530 A1 | 12/2009 | Yang |
| 2009/0324531 A1 | 12/2009 | Okada |
| 2009/0324532 A1 | 12/2009 | Okada |
| 2010/0143280 A1 | 6/2010 | Yokogi |
| 2010/0143281 A1 | 6/2010 | Okada |
| 2010/0143282 A1 | 6/2010 | Yokogi |
| 2010/0143425 A1* | 6/2010 | Okada et al. ............. 424/401 |
| 2011/0053826 A1 | 3/2011 | Wise |

FOREIGN PATENT DOCUMENTS

| | | |
|---|---|---|
| WO | WO9857615 A1 | 12/1998 |
| WO | WO99/62492 A1 | 12/1999 |
| WO | WO0000170 A1 | 1/2000 |
| WO | WO0040213 A1 | 7/2000 |
| WO | WO0117492 A1 | 3/2001 |
| WO | WO2004054693 A1 | 7/2004 |
| WO | WO2005070374 A1 | 8/2005 |
| WO | WO2005074868 A1 | 8/2005 |
| WO | WO2010052092 A1 | 5/2010 |

\* cited by examiner

MULTIPLE PRODUCT SYSTEM FOR HAIR COMPRISING A CONDITIONER WITH A SPECIFIC YIELD POINT

CROSS REFERENCE TO RELATED APPLICATION

This application claims the benefit of U.S. Provisional Application Ser. No. 61/184,053 filed Jun. 4, 2009.

FIELD OF THE INVENTION

The present invention relates to a multiple product system for keratinic material suitable for cleansing mammalian hair. The system presents a regimen for providing improved conditioning benefits.

BACKGROUND OF THE INVENTION

Conventional liquid compositions for keratinic material suitable for cleansing mammalian hair, such as shampoos and conditioners, are formulated to contain large amounts of water. The added weight and volume of this water significantly increases the costs of packaging, shipping, storing, and transporting these compositions. In addition, it increases the amount of energy used and the amount of waste generated.

It therefore would be desirable to provide a concentrated liquid personal cleansing composition that contains significantly less water than conventional compositions. Furthermore, it would be desirable for such a composition to have consumer-desired lathering and dissolution attributes. The multiple product system of the present invention provides improved silicone deposition leading to improved conditioning benefits, especially improved wet conditioning benefits after rinsing and improved dry conditioning after drying. It is desired to have a concentrated product regimen that does not sacrifice the desired end-use characteristics (e.g., good lather, easy to dissolve, appropriate stiffness and spreading properties) as a trade-off for a concentrated form.

A regimen of liquid compositions for keratinic material suitable for cleansing and conditioning mammalian hair in a concentrated form, among other things, should providing equal or better performance than traditional liquid compositions at ½ to ⅓ of the usage level of the traditional compositions, specifically for conditioning benefits. Therefore, in a compact form, the amount of carbon-generating resources required to formulate, package, and transport the composition

SUMMARY OF THE INVENTION

The present application relates to a multiple product system for keratinic material comprising the steps of applying from about 0.3 mL to about 0.67 mL per 10 g of hair of a hair cleaning composition comprising a dermatologically acceptable carrier, and from about 3% to about 40% of at least one surfactant selected from the group consisting of a branched and non-branched versions of decyl and undecyl alkyl sulfates which are either ethoxylated or non-ethoxylated; decyl alcohol modified lauryl sulfate; paraffin sulfonates with chain lengths ranging from $C_{13}$ to $C_{17}$; mixtures of linear and branched-chain alcohol sulfates with carbon chain lengths $C_{12}$ to $C_{17}$ which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates; and mixtures thereof; and about 0.05 wt % to about 10 wt % of a silicone emulsion; and applying from about 0.3 mL to about 0.67 mL per 10 g of hair of a hair conditioning composition comprising: a cationic surfactant; a high melting point fatty compound; and an aqueous carrier; wherein the hair conditioning composition has a yield point of at least 5 Pa, and the yield point meeting the following mathematical expression: $Y \geq 5.13X - 17.80$ wherein Y is yield point of the composition, X is a total amount (percentage by weigh of the composition) of the cationic surfactant and the high melting point fatty compound; and wherein the composition is substantially free of thickening polymers; wherein the application of the hair cleaning composition with or in series with the hair conditioning composition to keratinic material results in a silicone deposition of more than about 350 ppm.

DETAILED DESCRIPTION OF THE INVENTION

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

The term "topical application," as used herein, means to apply or spread the compositions of the present invention onto the surface of the keratinous tissue.

The present invention is a multiple product system for keratinic material suitable for cleansing mammalian hair. The multiple product system comprises compositions in a concentrated form, providing equal or better performance than traditional compositions of similar nature at ½ to ⅓ of the usage level.

A standard usage level of hair cleaning composition is from about 0.1 ml to about 2 ml per 10 g of hair, preferably from about 0.2 ml to about 1.5 ml per 10 g of hair. As such, a reduced or concentrated amount of the hair cleaning composition is from about 0.3 mL to about 0.67 mL; from about 0.067 mL to about 0.5 mL; from about 0.05 mL to about 1 mL; and from about 0.1 mL to about 0.75 mL per 10 g of hair.

A standard usage level of hair conditioning composition is from about 0.1 ml to about 2 ml per 10 g of hair, preferably from about 0.2 ml to about 1.5 ml per 10 g of hair. As such, a reduced or concentrated amount of the hair conditioning composition is from about 0.3 mL to about 0.67 mL; from about 0.067 mL to about 0.5 mL; from about 0.05 mL to about 1 mL; and from about 0.1 mL to about 0.75 mL per 10 g of hair.

The multiple product system of the present invention provides improved silicone deposition giving improved conditioning benefits, especially improved wet conditioning benefits after rinsing and improved dry conditioning after drying. The multiple product system of the present application may also provide improved product appearance to consumer. Thus, a reduced dosage of the discussed compositions of the present application may provide the same level of conditioning benefits as those of a full dosage of conventional shampoo and conditioner compositions.

Multiple Product System

The multiple product system comprises at least one hair cleaning composition as described herein and at least one hair conditioning composition as described herein. The two or more products are used as part of a regimen, preferably sequentially, to treat mammalian hair surfaces, preferably by topical application. The resulting silicone deposition on hair treated by the regimen is improved when the two or more products are utilized as part of a regimen, preferably sequentially, compared to when only one of either the hair cleaning composition or the hair conditioning composition is utilized alone or in combination with other products not meeting the elements described herein (herein referred to as conventional hair cleaning or conventional hair conditioning compositions).

For example, a hair cleaning composition according the present application used with a hair conditioning composition of the present application provides improved benefits such as silicone deposition compared to the hair cleaning composition utilized with a hair conditioning composition not described by the present application.

It is desired to have a concentrated product regimen that does not sacrifice the desired end-use characteristics (e.g., good lather, easy to dissolve, appropriate stiffness and spreading properties) as a trade-off for a concentrated form.

Hair Cleaning Composition

The hair cleaning compositions comprising relatively higher levels of surfactant compared to conventional hair cleaning composition may exhibit good rheology, lathering and dissolution properties because of the surfactants in the composition being in a middle or hexagonal phase. Therefore the hair cleaning compositions described herein comprise greater than about 23% isotropic surfactant and still provide good rheology, lather and dissolution.

The hair cleaning compositions herein are substantially free of organic solvent and/or hydrotrope. As used herein, "substantially free" means that the concentration of organic solvent and/or hydrotrope is no more than trace quantities that would be commonly found as an impurity in commercial ingredients. Because different organic solvents and/or hydrotropes can negatively impact rheology at differing magnitudes, the level at which any such material(s) is deemed to be at a "substantially free" concentration will depend upon the particular organic solvent and/or hydrotrope at issue. In one embodiment, the hair cleaning composition comprises less than about 0.2 wt % organic solvent or hydrotrope, in a particular embodiment from 0 wt % to about 0.2 wt % organic solvent or hydrotrope, and in some embodiments from 0 wt % to about 0.1 wt %.

As used herein, the terms "organic solvent" and "hydrotrope" encompass those materials recognized in the art as organic solvents or hydrotropes. Examples of organic solvents include those used in cleansing applications, and can be selected from the group consisting of alcohols, glycols, ethers, ether alcohols, and mixtures thereof. Typical hydrotropes can include cumene, xylene and toluene sulfonates, and mixtures thereof. Both solvent and hydrotrope examples are generally described in McCutcheon's, Detergents and Emulsifiers, North American edition (1986), published by Allured Publishing Corporation; and in McCutcheon's Functional Materials, North American Edition (1992).

Dermatologically Acceptable Carrier

The hair cleaning compositions of the present application comprise a dermatologically acceptable carrier for the composition. The carrier can be in a wide variety of forms. Non-limiting examples include simple solutions (water-based or oil-based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Emulsions that are utilized in the hair cleaning compositions can contain an aqueous phase and a lipid or oil. Lipids and oils may be derived from animals, plants, or petroleum and may be natural or synthetic (i.e., man-made). Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form.

The hair cleaning compositions can be in the form of pourable liquids (under ambient conditions). The hair cleaning compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

In accordance with at least some of the embodiments of the present application, the hair cleaning compositions can be in the form of pourable liquids (under ambient conditions). These compositions will therefore typically comprise an aqueous carrier, which is present at a level of from about 30% to about 97%, and alternatively from about 65% to about 90%.

Enabling Surfactant

In one embodiment, the composition comprises from about 3 wt % to about 40 wt %, alternatively from about 5 wt % to about 25 wt %, alternatively from about 10 wt % to about 20 wt %, alternatively from about 3 wt % to about 15 wt %, and alternatively from about 3 wt % to about 10% wt by weight of the composition, of at least one enabling surfactant.

The enabling surfactant(s) are carefully chosen based on three key parameters: 1) hydrophobic chainlength, 2) degree of branching in the hydrophobic chainlength, and 3) size of the surfactant head group as dictated by degree of ethoxylation; and combinations of these three parameters.

Without being limited by theory, the manipulation of these parameters allows the enabling surfactant to minimize surfactant phase structure (e.g., control appropriate phase behavior to produce less stringly micelles with no rods or more complex structures). Furthermore, the use of enabling surfactants in combination with any of a broad range of typical surfactants can provide good rheology, dissolution, and lather to compositions containing the enabling surfactant.

Examples of key enabling surfactant include, but are not limited to: branched and non-branched versions of decyl and undecyl alkyl sulfates which are either ethoxylated or non-ethoxylated; decyl alcohol modified lauryl sulfate; paraffin sulfonates with chain lengths ranging from $C_{13}$ to $C_{17}$ sold by the Clariant Company; mixtures of linear and branched-chain alcohol sulfates with carbon chain lengths $C_{12}$ to $C_{17}$ commonly known as LIAL® and NEODOL® alkyl or alcohol sulfates which are ethoxylated or non-ethoxylated; sodium salts of hydroxyethyl-2-dodecyl ether sulfates, or of hydroxyethyl-2-decyl ether sulfates (from Nippon Shokubai Inc., and either or both referred to herein as "NSKK ethoxy sulfate"); monoethoxylated lauryl alkyl sulfates; and mixtures thereof.

Decyl and Undecyl Sulfates

The decyl and undecyl sulfates of the hair cleaning composition of the multiple product system may be present from 0 wt % to about 6 wt %, preferably from about 0.1 wt % to about 6 wt % and comprise straight-chain decyl or undecyl sulfates having the formula (I): $R_1$—O($CH_2CHR_3O)_y$—$SO_3M$, branched-chain decyl undecyl sulfates having the general formula (II): $CH_3$—$(CH_2)_z$—$CHR_2$—$CH_2$—O($CH_2CHR_3O)_y$—$SO_3M$, or mixtures thereof, where $R_1$ of formula (I) represents $CH_3(CH_2)_9$ or $CH_3(CH_2)_{10}$, $R_2$ of formula (II) represents H or a hydrocarbon radical comprising 1 to 4 carbon atoms such that the sum of the carbon atoms in z of formula (II) and $R_2$ of formula (II) is 7 or 8, $R_3$ of formula (I) is H or $CH_3$, y of formulae (I) and (II) is 0 to 7, preferably 1 to 7, the average value of y of formulae (I) and (II) is 1 or less, preferably about 1, when y of formulae (I) and (II) is not equal to 0, and M of formulae (I) and (II) is a mono-valent or di-valent, positively-charged cation. Examples of mono-valent positively charged cations include ammonium, sodium, potassium, triethanolamine cation, and examples of di-valent positively charged cations include magnesium.

"Average value" is understood to mean that whereas the composition may comprise molecules having a value of y of formulae (I) and (II) other than 1, the average value of y of formulae (I) and (II) of all molecules in the composition is about 1. The undecyl sulfates may comprise from about 70% to about 90%, and alternatively about 80% of straight-chain undecyl sulfates and about 10% to about 30%, and alternatively about 20%, of branched-chain undecyl sulfates, by weight of the total amount of undecyl sulfates.

The undecyl sulfates of the hair cleaning composition of the multiple product system can be prepared by the hydroformylation of 1-decene or internal decenes, for example as described in U.S. Pat. No. 6,706,931, issued Mar. 16, 2004 to Shell Oil Company, to produce linear and branched primary alcohols which are sulfated with $SO_3$ in a falling film reactor and neutralized to make the alkylsulfuric acid salt, e.g. with sodium hydroxide to produce sodium undecyl sulfate. One example of a suitable alcohol is commercially available as NEODOL® 1 (Shell Oil Co.).

Additionally, the undecyl alcohol can be derived from castor soil via its hydrolysis to obtain ricinoleic acid. Ricinoleic can be pyrolyzed to obtain undecylenic acid. Undecylenic acid can be converted to undecyl alcohol via a series of hydrogenations to obtain undecyl alcohol.

The undecyl ethoxylates can be prepared by the addition of one molar equivalent of ethylene oxide or less to the undecyl alcohol in the presence of an alkaline catalyst. The resulting material may comprise from about 30 wt % to about 60 wt % by weight of the undecyl ethoxylates of unethoxylated alcohol, and the remaining mixture will consist of a variety of homologues with EO content ranging from 1 to 7. This mixture can be sulfated in a falling film reactor with $SO_3$ and neutralized with base, e.g. NaOH to produce the sodium undecyl alkoxy sulfates. Additionally, mixtures of the undecyl alcohol and undecyl alkoxylate can be blended together and sulfated as above to produce a mixture of undecyl-based surfactants.

Conditioning Agent

The hair cleaning compositions can comprise a conditioning agent, and in some embodiments at least about 0.05 wt % by weight of the hair cleaning compositions of a conditioning agent. In particular embodiments, the hair cleaning composition comprises from about 0.05 wt % to about 10 wt % by weight of the hair cleaning compositions conditioning agent, and in other embodiments from about 0.05 wt % to about 2 wt % by weight of the hair cleaning compositions, in alternate embodiments from about 0.5 wt % to about 10 wt % by weight of the hair cleaning compositions of a conditioning agent, and in still other embodiments from about 0.5 wt % to about 6 wt % by weight of the hair cleaning compositions of a conditioning agent.

Conditioning agents can include, for example, large and small particle silicone (e.g., small particle silicone of less than 0.1 microns), and oils. In one embodiment the silicone is an emulsion i.e., a separate, discontinuous phase of dispersed, insoluble droplets. These droplets are suspended with a suspending agent, numerous, nonexclusive suitable examples of which are described below.

The silicone conditioning agents preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, as measured at 25° C.

Optional silicone fluids include silicone oils which are flowable silicone materials having a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609.

The dispersed silicone conditioning agent particles typically have a number average particle diameter ranging from about 0.005 µm to about 50 µm. For small particle application to hair, the number average particle diameters typically range from about 0.01 µm to about 4 µm, commonly from about 0.01 µm to about 2 µm, generally from about 0.01 µm to about 0.5 µm. For larger particle application to hair, the number average particle diameters typically range from about 4 µm to about 50 µm, commonly from about 6 µm to about 30 µm, generally from about 9 µm to about 20 µm, typically from about 12 µm to about 18 µm.

Background material on silicones including sections discussing silicone fluids, gums, and resins, as well as manufacture of silicones, are found in Encyclopedia of Polymer Science and Engineering, vol. 15, 2d ed., pp 204 308, John Wiley & Sons, Inc. (1989).

Anionic Surfactants

The hair cleaning composition of the present application may comprise from 0 wt % to about 30%, of additional anionic surfactants, alternatively from about 0.1 wt % to about 30 wt %, alternatively from about 0.1 wt % to about 10 wt %, alternatively from about 10 wt % to about 20 wt % of additional anionic surfactants. Additional anionic surfactants suitable for use herein include alkyl and alkyl ether sulfates of the formula (III) $ROSO_3M$ and $RO(C_2H_4O)_xSO_3M$, wherein R of formula (III) is alkyl or alkenyl of from about 8 to about 18 carbon atoms, x of formula (III) is 1 to 10, and M of formula (III) is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 18 carbon atoms. The alcohols can be derived from fats, e.g., coconut oil, palm oil, palm kernel oil, or tallow, or can be synthetic.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

Co-Surfactants

Co-surfactants are materials which are combined with anionic surfactants discussed herein to enhance lather volume and/or to modify lather texture of the hair cleaning composition of the multiple product system. Typically these materials can be selected from a variety of families of structures including, but not limited to, amphoteric, zwitterionic, cationic, and nonionic. They are typically used with anionic surfactants in a weight ratio of 1:20 to 1:4, more preferably in the 1:12 to 1:7 weight ratio.

The hair cleaning composition of the present application may comprise from about 0.5 wt % to about 10 wt %, alternatively from about 0.5 wt % to about 5 wt %, and alternatively from about 1 wt % to about 3 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The family of amphoacetates derived from the reaction of sodium chloroacetate with amidoamines to produce alkanoyl amphoacetates are particularly effective, e.g. lauryolamphoacetate, and the like.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl)sulfopropyl betaine and mixtures thereof. Also suitable zwitterionic surfactants include amidobetaines and amidosulfobetaines, wherein the $RCONH(CH_2)_3$ radical, wherein R is a $C_{11}$-$C_{17}$ alkyl, is attached to the nitrogen atom of the betaine are also useful in this application.

Nonionic co-surfactants typically used in the hair cleaning composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or $C_{12}$ alpha olefins with ethylene glycol (e.g., hydroxyethyl-2-decyl ether, hydroxyethyl-2-dodecyl ether), as can be made according to the teachings of U.S. Pat. No. 5,741,948; U.S. Pat. No. 5,994,595; U.S. Pat. No. 6,346,509; and U.S. Pat. No. 6,417,408.

Other preferred nonionic surfactants may be selected from the group consisting of glucose amides, alkyl polyglucosides, sucrose cocoate, sucrose laurate, alkanolamides, ethoxylated alcohols (distinguished from the Enabling Surfactant) and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

In a particular embodiment, the co-surfactant is selected from the group consisting of cocomonoethanol amide, cocoamidopropyl betaine, laurylamidopropyl betaine, cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidopropyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

Cationic Polymer

The hair cleaning compositions can comprise a cationic polymer, and in some embodiments at least about 0.05 wt % by weight of the hair cleaning compositions of a cationic polymer. In particular embodiments, the hair cleaning composition comprises from about 0.05 wt % to about 10 wt % by weight of the hair cleaning compositions of a cationic polymer, and in other embodiments from about 0.05 wt % to about 2 wt % by weight of the hair cleaning compositions, in alternate embodiments from about 0.5 wt % to about 10 wt % by weight of the hair cleaning compositions of a cationic polymer, and in still other embodiments from about 0.5 wt % to about 6 wt % by weight of the hair cleaning compositions of a cationic polymer.

A suitable cationic polymer will have a cationic charge density of at least about 0.3 meq/gm, typically at least about 0.5 meq/gm, commonly at least about 0.7 meq/gm, but also generally less than about 7 meq/gm, typically less than about 5 meq/gm, at the pH of intended use of the hair cleaning composition. The pH of intended use of the composition generally ranges from about pH 3 to about pH 9, typically from about pH 4 to about pH 8. A suitable cationic polymer will generally have an average molecular weight ranging from about 1,000 to about 10,000,000, typically from about 10,000 to about 5,000,000, commonly about 20,000 to about 2,000,000.

The term "charge density", as used herein, refers to the ratio of the number of positive charges on a polymer to the molecular weight of said polymer.

Suitable cationic polymers for use in the hair cleaning compositions can contain cationic nitrogen-containing moieties such as quaternary ammonium or cationic protonated amino moieties. The cationic protonated amines can be primary, secondary, or tertiary amines (typically secondary or tertiary), depending upon the particular species and the selected pH of the composition. Any anionic counterions can be used in association with the cationic polymers so long as the polymers remain soluble in water, in the hair conditioning composition, or in a coacervate phase of the hair conditioning composition, and so long as the counterions are physically and chemically compatible with the components of the hair conditioning composition or do not otherwise unduly impair product performance, stability or aesthetics. Non-limiting examples of such counterions include halides (e.g., chloride, fluoride, bromide, iodide), sulfate and methylsulfate.

Non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)). Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium-6 and Polyquaternium-7, respectively); amphoteric copolymers of acrylic acid including copolymers of acrylic acid and dimethyldiallylammonium chloride (referred to in the industry by CTFA as Polyquaternium-22), terpolymers of acrylic acid with dimethyldiallylammonium chloride and acrylamide (referred to in the industry by CTFA as Polyquaternium-39), and terpolymers of acrylic acid with methacrylamidopropyl trimethylammonium chloride and methylacrylate (referred to in the industry by CTFA as Polyquaternium-47). Suitable cationic substituted monomers are the cationic substituted dialkylaminoalkyl acrylamides, dialkylaminoalkyl methacrylamides, and combinations thereof. These suitable monomers conform to the formula (IV):

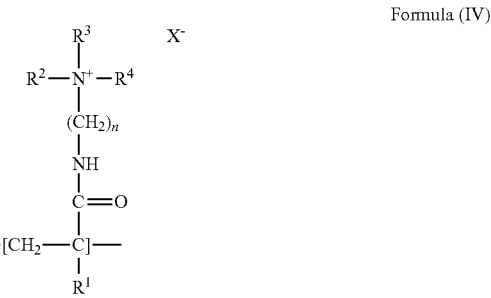

Formula (IV)

wherein $R^1$ of formula (IV) is hydrogen, methyl or ethyl; each of $R^2$, $R^3$, and $R^4$ of formula (IV) are independently hydrogen or a short chain alkyl having from about 1 to about 8 carbon atoms, typically from about 1 to about 5 carbon atoms, commonly from about 1 to about 2 carbon atoms; n of formula (IV) is an integer having a value of from about 1 to about 8, typically from about 1 to about 4; and X of formula (IV) is a counterion. The nitrogen attached to $R^2$, $R^3$, and $R^4$ of formula (IV) may be a protonated amine (primary, secondary, or tertiary), but is typically a quaternary ammonium wherein each of $R^2$, $R^3$, and $R^4$ of formula (IV) are alkyl groups, a non-limiting example of which is polymethyacrylamidopropyl trimonium chloride, available under the trade name POLYCARE® 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula (V):

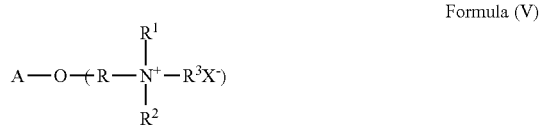

Formula (V)

wherein A of formula (V) is an anhydroglucose residual group, such as a starch or cellulose anhydroglucose residual; R formula (V) is an alkylene oxyalkylene, polyoxyalkylene, or hydroxyalkylene group, or combination thereof; $R^1$, $R^2$, and $R^3$ formula (V) independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$, and $R^3$ formula (V)) typically being about 20 or less; and X formula (V) is an anionic counterion as described hereinbefore.

Suitable cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp., under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc.

Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581.

When used, the cationic polymers herein are either soluble in the composition or are soluble in a complex coacervate phase in the composition formed by the cationic polymer and the detersive surfactant components described hereinbefore. Complex coacervates of the cationic polymer can also be formed with other charged materials in the composition.

Cationic polymers useful herein may include those discussed in US 2007/0207109 A1 and US 2008/0206185 A1, such as synthetic copolymer of sufficiently high molecular weight to effectively enhance the deposition of the conditioning active components of the personal care composition described herein. Combinations of cationic polymer may also be utilized. The average molecular weight of the synthetic copolymers is generally between about 10,000 and about 10 million, preferably between about 100,000 and about 3 million, still more preferably between about 200,000 and about 2 million.

In a further embodiment, the synthetic copolymers have mass charge densities of from about 0.1 meq/gm to about 6.0 meq/gm and more preferably from about 0.5 meq/gm to about 3.0 meq/gm, at the pH of intended use of the personal care composition. The pH will generally range from about pH 3 to about pH 9, and more preferably between about pH 4 and about pH 8.

In yet another embodiment, the synthetic copolymers have linear charge densities from at least about 2 meq/A to about 500 meq/A, and more preferably from about 20 meq/A to about 200 meq/A, and most preferably from about 25 meq/A to about 100 meq/A.

Cationic polymer may be copolymers or homopolymers. In one embodiment, a homopolymer is utilized in the present composition. In another embodiment, a copolymer is utilized in the present composition. In another embodiment a mixture of a homopolymer and a copolymer is utilized in the present composition. In another embodiment, a homopolymer of a naturally derived nature, such as cellulose or guar polymer discussed herein, is combined with a homopolymer or copolymer of synthetic origin, such as those discussed below.

Homopolymers—Non-crosslinked cationic homopolymers of the following monomers are also useful herein: 3-acrylamidopropyltrimethylammonium chloride (APTAC), diallyldimethylammonium chloride (DADMAC), [(3-methylacrylolyamino)propyl]trimethylammonium chloride (MAPTAC), 3-methyl-1-vinylimidazolium chloride (QVI); [2-(acryloyloxy)ethyl]trimethylammonium chloride and [2-(acryloyloxy)propyl]trimethylammonium chloride.

Copolymers—copolymer may be comprises of two cationic monomer or a nonionic and cationic monomers.

Nonionic Monomer Unit

A copolymer suitable for use herein comprises a nonionic monomer unit represented by the following Formula (VI): I.

Formula (VI)

where R of formula (VI) is H or $C_{1-4}$ alkyl; and $R^1$ and $R^2$ of formula (VI) are independently selected from the group consisting of H, $C_{1-4}$ alkyl, $CH_2OCH_3$, $CH_2OCH_2CH(CH_3)_2$, and phenyl, or together are $C_{3-6}$ cycloalkyl.

In one embodiment, nonionic monomer unit is acrylamide (AM), i.e., where R, $R^1$, and $R^2$ of formula (VI) are H as shown below in formula (VII):

Formula (VII)

where m is equal to 1.

Another preferred nonionic monomer unit is methacrylamide (MethAM), i.e., where R of formula (VI) is $C_1$ alkyl, and $R^1$ and $R^2$ of formula (VIII) are each H:

Formula (VIII)

where m is equal to 1.

However, the other acrylamide derivatives within the scope of the formula set out above are also contemplated to be suitable where polyacrylamide and copolymers using acrylamide monomers are useful.

The nonionic monomer portion of the copolymer may be present in an amount from about 50 wt % to about 99.5 wt % by weight of the total copolymer. Preferably, this amount is from about 70 wt % to about 99 wt %, still more preferably from about 80 wt % to about 99 wt % by weight of copolymer.

Cationic Monomer Unit

The copolymers may also comprise a cationic monomer unit represented by Formula (IX):

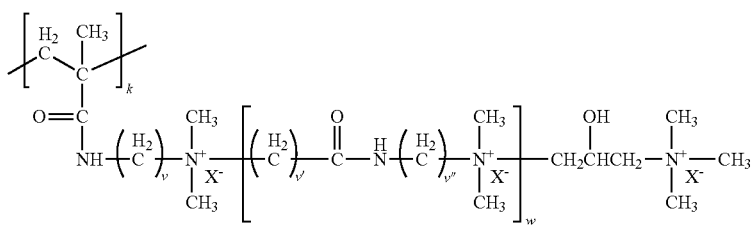

Formula (IX)

where k of formula (IX) is 1, each of v, v', and v" of formula (IX) is independently an integer of from 1 to 6, w of formula (IX) is zero or an integer of from 1 to 10, and $X^-$ of formula (IX) is an anion.

In one embodiment, a structure is present where k=1, v=3 and w=0 and $X^-$ is $Cl^-$ according to formula (IX), above, to form the following structure:

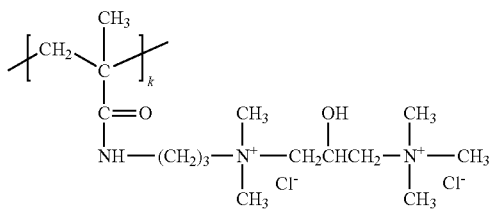

Formula (X)

The above structure may be referred to as diquat.

Yet another embodiment is achieved by the structure formed wherein k=1, v and v" are each 3, v'=1, w=1, and $X^-$ is $Cl^-$ according to formula (IX), such as:

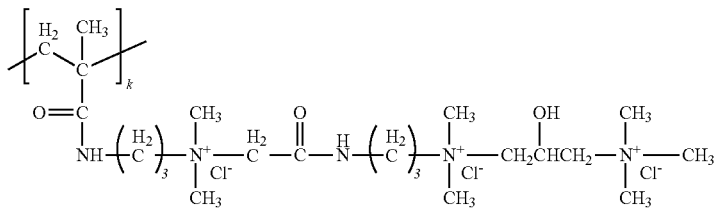

Formula (XI)

The above structure may be referred to as triquat.

Suitable cationic monomers can be made by, for example, the methods described in U.S. Patent Application Publication No. 2004/0010106 A1.

Optional Ingredients

The compositions of the present application may include a broad range of additional components, depending on the product form and its intended use and end benefit. In one embodiment, individual concentrations of such optional components may range from about 0.001 wt % to about 50 wt %, and in another embodiment from about 0.001 wt % to about 10 wt % by weight of the composition.

Non-limiting examples of optional components for use in compositions of the present application are described in U.S. Pat. No. 6,335,312, issued to Coffindaffer et al. and include anti dandruff agents (such as piroctone olamine, water insoluble components such as 3,4,4'-trichlorocarbanilide (trichlosan), triclocarban and zinc pyrithione), antiseborrheic agents, antipsoriasis agents, oxidative dye precursors, developers, oxidizing agents, alkalizing agents, suspending agents, viscosity modifiers, anti-static agents, humectants, emollients, suspending agents, viscosity modifiers, antimicrobial agents, sequestrants, proteins, skin care actives, sunscreens, UV absorbers, vitamins and other aesthetic components such as essential oils, skin sensates, astringents, skin soothing agents, skin healing agents and the like, nonlimiting examples of which include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate, derivatives of any of the foregoing and combinations thereof.

Anti-Dandruff Actives—The hair cleaning compositions of the present application may also contain an anti-dandruff agent. Suitable, non-limiting examples of anti-dandruff particulates include: pyridinethione salts, zinc-containing layered material, azoles, such as ketoconazole, econazole, and elubiol, selenium sulfide, particulate sulfur, salicylic acid and mixtures thereof. A typical anti-dandruff particulate is pyridinethione salt. Such anti-dandruff particulate should be physically and chemically compatible with the components of the composition, and should not otherwise unduly impair product stability, aesthetics or performance.

Pyridinethione anti-dandruff particulates, especially 1-hydroxy-2-pyridinethione salts, are suitable particulate anti-dandruff agents for use in compositions of the present application. The concentration of pyridinethione anti-dandruff particulate typically ranges from about 0.01 wt % to about 5 wt %, by weight of the composition, generally from about 0.1 wt % to about 3 wt %, commonly from about 0.1 wt % to about 2 wt %. Suitable pyridinethione salts include those formed from heavy metals such as zinc, tin, cadmium, magnesium, aluminum and zirconium, generally zinc, typically the zinc salt of 1-hydroxy-2-pyridinethione (known as "zinc pyridinethione" or "ZPT"), commonly 1-hydroxy-2-pyridinethione salts in platelet particle form, wherein the particles have an average size of up to about 20µ, typically up to about 5µ, commonly up to about 2.5µ. Salts formed from other cations, such as sodium, may also be suitable. Pyridinethione anti-dandruff agents are described, for example, in U.S. Pat. No. 2,809,971; U.S. Pat. No. 3,236,733; U.S. Pat. No. 3,753, 196; U.S. Pat. No. 3,761,418; U.S. Pat. No. 4,345,080; U.S. Pat. No. 4,323,683; U.S. Pat. No. 4,379,753; and. U.S. Pat. No. 4,470,982.

Zinc-Containing Layered Material

In an embodiment of the present application, the composition may include an effective amount of a zinc-containing layered material. Preferred embodiments of the present application include from about 0.001 wt % to about 10 wt % of a zinc-containing layered material; more preferably from about 0.01 wt % to about 7 wt %; more preferably still from about 0.1 wt % to about 5 wt %.

Examples of zinc-containing layered materials useful in certain embodiments of the present application include those discussed in US 2004/0223941 A1 (e.g., basic zinc carbonate); Crepaldi, E L, Pava, P C, Tronto, J, Valim, J B *J. Colloid Interfac. Sci.* 2002, 248, 429-42; and Morioka, H., Tagaya, H., Karasu, M, Kadokawa, J, Chiba, K *Inorg. Chem.* 1999, 38, 4211-6.

Anti-dandruff efficacy can be increased in topical compositions by the use of polyvalent metal salts of pyrithione, such as zinc pyrithione, in combination with zinc-containing layered materials. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"); more preferably ZPT in platelet particle form, wherein the particles have an average size of up to about 20 µm, preferably up to about 5 µm, more preferably up to about 2.5 µm.

A zinc-containing layered material with a solubility of less than 25% will have a measurable % soluble zinc value below a threshold value determined by the weight percent and molecular weight of the zinc compound. The theoretical threshold value can be calculated as discussed in US 2003/0215522 A1.

Hair Conditioning Composition

The hair conditioning composition of the present application comprises a cationic surfactant; a high melting point fatty compound; and an aqueous carrier where the hair conditioning composition have the following properties:

wherein the composition has a yield point of at least 5 Pa, and the yield point meeting the following mathematical expression:

$$Y \geq 5.13X - 17.80$$

wherein Y is yield point of the composition, X is a total amount (percentage by weigh of the composition) of the cationic surfactant and the high melting point fatty compound;

and wherein the composition is substantially free of thickening polymers.

Yield Point

The yield point of the present application is measured by dynamic oscillation stress sweep at 1 Hz frequency and 25° C., by means of a rheometer available from TA Instruments with a mode name of AR2000 using 40 mm diameter parallel type geometry having gap of 1000 µm.

The composition of the present invention has a yield point of about 5 Pa or more, preferably 8 Pa or more, in view of providing a desired rheology as marketed product and product stability.

Preferably, in view of providing improved wet conditioning benefits after rinsing, and improved dry conditioning, the composition of the present invention has a yield point of about 33 Pa or more preferably about 35 Pa or more, more preferably 40 Pa or more. The above yield point may be also preferred in view of providing richer, thicker, and/or more concentrated product appearance.

Gel Matrix

The hair conditioning composition comprises a gel matrix including lamella gel matrix. The gel matrix comprises the cationic surfactant, the high melting point fatty compound, and an aqueous carrier. The gel matrix is suitable for providing various conditioning benefits, such as slippery feel during the application to wet hair and softness and moisturized feel on dry hair.

In view of providing improved wet conditioning benefits, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:4, still more preferably from about 1:2 to about 1:4.

Preferably, in view of stability of the gel matrix, the hair conditioning composition is substantially free of anionic surfactants and anionic polymers. In the hair conditioning composition, "substantially free of anionic surfactants and anionic polymers" means that the composition contains 1 wt % or less, preferably 0.5 wt % or less, more preferably totally 0 wt % of total of anionic surfactants and anionic polymers.

D-Spacing

The hair conditioning composition herein is characterized by the combination of the above specific conversion rate and specific yield point provide improved wet performance, especially wet conditioning after rinsing, even if such hair conditioning composition having a larger d-spacing than those of the compositions of WO 2006/044209. Such larger d-spacing herein means a d-spacing of above 33 nm (excluding 33 nm). D-spacing in the present application means a distance between two lamellar bilayers plus the width of one lamellar bilayer, in lamellar gel matrix, as shown in Fig. 1. Thus, d-spacing is defined according to the following equation:

$$D\text{-spacing} = d_{water} + d_{bilayer}$$

D-spacing can be measured by using a High Flux Small Angle X-ray Scattering Instrument available from PANalytical with a tradename SAXSess, under the typical conditions of Small Angle X-Ray Scattering (SAXS) measurements in a q-range ($q = 4\pi/\lambda \sin(\theta)$ wherein $\lambda$ is the wavelength and $\theta$ is half the scattering angel) of $0.06 < q/nm^{-1} < 27$ which corresponds to $0.085 < 2\theta/degree < 40$. All data are transmission-calibrated by monitoring the attenuated primary beam intensity and normalizing it into unity, so that relative intensity for different samples can be obtained. The transmission-calibration allows us to make an accurate subtraction of water contribution from the net sample scattering. D-spacing is calculated according to the following equation (which is known as Bragg's equation): $n\lambda = 2d \sin(\theta)$, wherein n is the number of lamellar bi-layers.

The total amount of the cationic surfactant and the high melting point fatty compound is, preferably from about 4 wt %, more preferably from about 4.5 wt %, still more preferably from about 5 wt % by weight of the composition, in view of providing the benefits of the present application, and to about 15 wt %, preferably to about 14 wt %, more preferably to about 13 wt %, still more preferably to about 10 wt % by weight of the composition, in view of spreadability and product appearance.

The hair conditioning composition is substantially free of thickening polymers. It is believed that the addition of thickening polymer reduces spreadability of the products. In the present application, "the composition being substantially free of thickening polymers" means that: the hair conditioning composition is free of thickening polymers; or, if the hair conditioning composition contains a thickening polymer, the level of such thickening polymer is very low. The level of such thickening polymers, if included, 1 wt % or less, preferably 0.5 wt % or less, more preferably 0.1 wt % or less, still more preferably 0.06 wt % by weight of the hair conditioning composition. Most preferably, the level of such thickening polymer is 0 wt % by weight of the hair conditioning composition. Such thickening polymers include, for example, guar polymers including nonionic and cationic guar polymers, cellulose polymers including nonionic, cationic, and/or hydrophobically modified cellulose polymers such as cetyl hydroxyethylcellulose, other synthetic polymers including nonionic and cationic synthetic polymers such as polyquaternium-37.

Cationic Surfactant

The hair conditioning composition comprises a cationic surfactant. The cationic surfactant can be included in the hair conditioning composition at a level from about 0.1 wt %, preferably from about 0.5 wt %, more preferably from about 1.0 wt %, still more preferably from about 1.5 wt %, and to about 8 wt %, preferably to about 5 wt %, more preferably to about 4 wt % by weight of the hair conditioning composition.

It is preferred in the hair conditioning composition, in view of improved wet conditioning benefits, the hair conditioning composition is substantially free of other cationic surfactants than those described herein. Such "other cationic surfactant" includes, for example, tertiary amines, tertiary amine salts, and di-long alkyl quaternized ammonium salts. In the hair conditioning composition, "substantially free of other cationic surfactants" means that the hair conditioning composition contains 1 wt % or less, preferably 0.5 wt % or less, more preferably totally 0 wt % of total of such other cationic surfactants.

One of the preferred cationic surfactants of the hair conditioning composition is a salt of a mono-long alkyl quaternized ammonium and an anion, wherein the anion is selected from the group consisting of halides such as chloride and bromide, $C_1$-$C_4$ alkyl sulfate such as methosulfate and ethosulfate, and mixtures thereof. More preferably, the anion is selected from the group consisting of halides such as chloride and mixtures thereof.

The mono-long alkyl quaternized ammonium salts useful herein are those having the formula (XII):

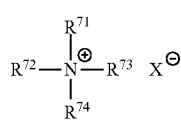

formula (XII)

wherein one of $R^{71}$, $R^{72}$, $R^{73}$ and $R^{74}$ of formula (XII) is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ of formula (XII) are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ of formula (XII) is a salt-forming anion selected from the group consisting of halides such as chloride and bromide, $C_1$-$C_4$ alkyl sulfate such as methosulfate and ethosulfate, and mixtures thereof.

The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ of formula (XII) is selected from an alkyl group of from 16 to 40 carbon atoms, more preferably from 18 to 26 carbon atoms, still more preferably from 22 carbon atoms; and the remainder of $R^{71}$, $R^{72}$, $R^{73}$ and $R^{74}$ of formula (XII) are independently selected from $CH_3$, $C_2H_5$, $C_2H_4OH$, $CH_2C_6H_5$, and mixtures thereof.

Among them, more preferred cationic surfactants are those having a longer alkyl group, i.e., $C_{18-22}$ alkyl group. Such cationic surfactants include, for example, behenyl trimethyl ammonium chloride, methyl sulfate or ethyl sulfate, and stearyl trimethyl ammonium chloride, methyl sulfate or ethyl sulfate. Further preferred are behenyl trimethyl ammonium chloride, methyl sulfate or ethyl sulfate, and still further preferred is behenyl trimethyl ammonium chloride.

The high melting point fatty compound can be included in the hair conditioning composition at a level of from about 1.0 wt %, preferably from about 1.5 wt %, more preferably from about 2.0 wt %, still more preferably from about 4.0 wt %, and to about 15 wt %, preferably to about 10 wt % by weight of the hair conditioning composition.

The high melting point fatty compound useful herein have a melting point of 25° C. or higher, preferably 40° C. or higher, more preferably 45° C. or higher, still more preferably 50° C. or higher, in view of stability of the gel matrix. Preferably, such melting point is up to about 90° C., more preferably up to about 80° C., still more preferably up to about 70° C., even more preferably up to about 65° C., in view of easier manufacturing and easier emulsification. In the hair conditioning composition, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the hair conditioning composition. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

In the present application, more preferred fatty alcohols are cetyl alcohol, stearyl alcohol and mixtures thereof.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan).

The hair conditioning composition comprises an aqueous carrier. The level and species of the carrier are selected according to the compatibility with other components, and other desired characteristic of the product.

The carrier useful in the present application includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the hair conditioning composition comprise from about 20 wt % to about 99 wt %, preferably from about 30 wt % to about 95 wt %, and more preferably from about 80 wt % to about 90 wt % by weight of the hair conditioning composition of water.

Preferably, the hair conditioning composition preferably contains a silicone compound. It is believed that the silicone compound can provide smoothness and softness on dry hair. The silicone compounds herein can be used at levels by weight of the composition of preferably from about 0.1 wt % to about 20 wt %, more preferably from about 0.2 wt % to about 10 wt %, still more preferably from about 0.2 wt % to about 5 wt % by weight of the hair conditioning composition.

Preferably, the silicone compounds have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their VISCASIL® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (XIII):

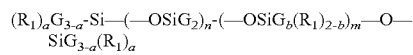

$(R_1)_a G_{3-a}\text{-Si}\text{—}(\text{—OSiG}_2)_n\text{-}(\text{—OSiG}_b(R_1)_{2-b})_m\text{—O—SiG}_{3-a}(R_1)_a$ wherein G of formula (XII) is hydrogen, phenyl, hydroxy, or $C_1$-$C_8$ alkyl, preferably methyl; a of formula (XII) is 0 or an integer having a value from 1 to 3, preferably 1; b of formula (XII) is 0, 1 or 2, preferably 1; n of formula (XII) is a number from 0 to 1,999; m of formula (XII) is an integer from 0 to 1,999; the sum of n and m is a number from 1 to 2,000; a and m are not both 0; $R_1$ of formula (XII) is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—NR$_2$H$_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion.

Highly preferred amino silicones are those corresponding to formula (XIII) wherein m=0, a=1, q=3, G=methyl, n is preferably from about 1500 to about 1700, more preferably about 1600; and L is —N($CH_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N($CH_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the hair conditioning composition, can be mixed with solvent having a lower viscosity. Such solvents include, for example, polar or non-polar, volatile or non-volatile oils. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the hair conditioning composition in the form of an emulsion, wherein the emulsion is made by mechanical mixing, or in the stage of synthesis through emulsion polymerization, with or without the aid of a surfactant selected from anionic surfactants, nonionic surfactants, cationic surfactants, and mixtures thereof.

Method of Manufacturing Hair Conditioning Composition

The hair conditioning composition is preferably prepared by a method comprising the steps:
(1) preparing an oil phase comprising the surfactant and the high melting point fatty compound, wherein the temperature of the oil phase is higher than a melting point of the high melting point fatty compound; and
(2) preparing an aqueous phase comprising the aqueous carrier, wherein the temperature of the aqueous phase is below the melting point of the high melting point fatty compounds; and
(3) mixing the oil phase and the aqueous phase to form an emulsion; wherein the mixing step (3) comprises the following detailed steps:
(3-1) feeding either of the oil phase or the aqueous phase into a high shear field having an energy density of about $1.0 \times 10^2$ $J/m^3$ or more;
(3-2) feeding the other phase directly to the field; and
(3-3) forming an emulsion;
and the method further requires at least one of the following:
the mixing step (3) is conducted by using a homogenizer having a rotating member;
the surfactant is a mono-alkyl cationic surfactant and the composition is substantially free of di-alkyl cationic surfactants; and
the surfactant is a cationic surfactant and the oil phase contains from 0 to about 50% of the aqueous carrier by weight of the oil phase, preferably the oil phase is substantially free of water.

Details of Mixing Step (3)

In the present application, by directly feeding the discussed oil and aqueous phase to the high shear field, the oil phase and the aqueous phase first meet in the high shear field. It is believed that, by meeting first in the high shear field, an improved transformation of surfactants and high melting point fatty compounds to emulsions results, i.e., the resulted hair conditioning compositions contain reduced amount of non-emulsified surfactants/high melting point fatty compounds, compared to other methods by which such phases first meet in non- or lower shear field. It is also believed that, by such improved transformation to an emulsion, the method of the present application provides the resulted hair conditioning composition with improved conditioning benefits, and may also provide them with improved product appearance and/or product stability.

In the present application, "direct feeding" means, feeding the two phases such that the two phases can reach to the high shear field after first meeting, within 0.3 seconds or less, preferably 0.2 seconds or less, more preferably 0.1 seconds or less, still more preferably 0 second, in view of improved transforming to emulsions. In the present application, the direct feeding is preferably conducted by a direct injection.

In the present application, "high shear field" means that the field has an energy density of from about $1.0 \times 10^2$ $J/m^3$, preferably from about $1.0 \times 10^3$ $J/m^3$, more preferably from about $1.0 \times 10^4$ $J/m^3$ in view of improved transforming to emulsions, and to about $5.0 \times 10^8$ $J/m^3$, preferably to about $2.0 \times 10^7$ $J/m^3$, more preferably to about $1.0 \times 10^7$ $J/m^3$ in view of stably manufacturing the hair conditioning compositions with improved transformation.

In the present application, it is preferred that the mixing step (3) comprises the following detailed steps:
(3-1) feeding the aqueous phase into a high shear field having an energy density of $1.0 \times 10^2$ $J/m^3$ or more;
(3-2) feeding the oil phase directly to the field; and
(3-3) forming an emulsion.

In the present application, especially when using homogenizers having a rotating member described below in detail, it is preferred to feed the oil phase into the high shear field in which the aqueous phase is already present, in view of stably manufacturing the hair conditioning compositions with improved conditioning benefits.

Preferably, in the present application, the mixing step (3) including the detailed steps (3-1) and (3-2) is conducted by using a high shear homogenizer. High shear homogenizers useful herein include, for example: homogenizers having a rotating member such as BECOMIX® available from A. Berents Gmbh&Co., which is a direct injection, rotor-stator homogenizer, and Lexa-30 available from Indolaval/Tetra-Pac, which is a direct injection, rotor-stator homogenizer; and high pressure homogenizers such as SONOLATOR® available from Sonic Corporation, which is a high pressure ultrasonic homogenizer.

These high shear homogenizers are preferred since the two phases (oil and aqueous) can quickly reach to the high shear field after first meeting, compared to other high shear homogenizers such as Manton Gaulin type homogenizer available from the APV Manton Corporation, Microfluidizer available from Microfluidics Corporation, T. K. pipeline homomixer available from Primix Corporation, and DR-3 available from IKA Corporation, when used as-is. Those other high shear homogenizers might be used with modifications such that the two phases can quickly reach to the high shear field after first meeting.

In the present application, homogenizers having a rotating member, especially direct injection, rotor-stator homogenizers are preferred, rather than high pressure homogenizers such as SONOLATOR® available from Sonic Corporation which is normally operated with a higher energy density of about $5.0 \times 10^7$ $J/m^3$, in view of manufacturing stability, i.e., stably providing hair conditioning compositions with improved conditioning benefits.

Method of Use

The regimen of the present application is used for a method of cleaning and conditioning hair, the method comprising following steps:
(i) wetting hair and applying an effective amount of the hair cleaning composition;
(ii) rinsing the hair;
(iii) applying to the hair an effective amount of the conditioning composition for conditioning the hair; and
(ii) rinsing the hair.

Effective amount herein is, for example, from about 0.3 mL to about 0.67 mL; from about 0.067 mL to about 0.5 mL; from about 0.05 mL to about 1 mL; and from about 0.1 mL to about 0.75 mL per 10 g of hair.

The multiple product regimen of the present application provides improved conditioning benefits, especially improved wet conditioning benefits after rinsing and improved dry conditioning, while maintaining wet conditioning benefit before rinsing. A reduced dosage of the hair cleaning composition and conditioning composition of the present application may provide the same level of conditioning benefits as those of a full dosage of conventional shampoo and conventional conditioner compositions. Such reduced dosage herein is, for example, from about 0.3 ml to about 0.7 ml per 10 g of hair.

Wet and Dry Conditioning Test Methods

Wet Conditioning During Conditioner Spreading

Wet conditioning before rinsing is evaluated by hair friction force measured by an instrument named Texture Analyzer (TA XT Plus, Texture Technologies, Scarsdale, N.Y., USA). 1 g of the composition is applied to 10 g of hair sample. After spreading the composition on the hair sample and before rinsing it, friction force (g) between the hair sample and a polyurethane pad is measured by the above instrument.

A: Above 5% (excluding 5%) to 10% reduction of Friction force, compared to Control B: Up to 5% (including 5%) reduction of Friction force, compared to Control C: Control or Equal to Control D: Increased Friction force, compared to Control Wet Conditioning During Conditioner Rinsing Wet conditioning after rinsing is evaluated by hair friction force measured by an instrument named Texture Analyzer (TA XT Plus, Texture Technologies, Scarsdale, N.Y., USA). 1 g of the composition is applied to 10 g of hair sample. After spreading the composition on the hair sample, rinsing it with warm water for 30 seconds. Then, friction force (g) between the hair sample and a polyurethane pad is measured by the above instrument.

A: Above 5% (excluding 5%) to 10% reduction of Friction force, compared to Control B: Up to 5% (including 5%) reduction of Friction force, compared to Control C: Control or Equal to Control D: Increased Friction force, compared to Control Dry Conditioning Dry conditioning performance is evaluated by hair friction force measured by an instrument named Instron Tester (Instron 5542, Instron, Inc.; Canton, Mass., USA). 2 g of the composition is applied to 20 g of hair sample. After spreading the composition on the hair sample, rinsing it with warm water for 30 seconds, and the hair sample is left to dry over night. The friction force (g) between the hair surface and a urethane pad along the hair is measured.

A: Above 5% (excluding 5%) to 10% reduction of Friction force, compared to Control B: Up to 5% (including 5%) reduction of Friction force, compared to Control C: Control or Equal to Control D: Increased Friction force, compared to Control Hair Substrate Preparation Method Two different hair substrates of differing polarities are required upon which to measure silicone deposition, and thereby also calculate a value for deposition evenness across the two substrates. Hair is supplied by Hugo Royer International Limited (10 Lakeside Business Park, Sandhurst, Berkshire, GU47 9DN, England) and is a blended, Eastern European, mid-brown human hair. Prior to use, the hair is assessed and qualified for low cuticular damage (<20%) and misalignment (<5%), based on at least 200 hair strands per batch. Any damage on a hair strand counts as one point damaged, and then the total is calculated as a percentage. This hair is made into 4" (10 cm), 2 g round tied switches (where the length and weight of hair corresponds to the hair below the tie). To obtain hair substrates with two distinct polarities this hair is then pre-treated according to one of two distinct protocols.

Virgin Hair Preparation

Hair switches are washed in a sink fitted with a shower attachment set with a flow rate of 6±1 L min$^{-1}$ and a temperature of 37±2° C. using the following protocol: switches are initially wetted under the shower attachment for 30 s. The hair is then removed from the water flow and 0.2 g of shampoo (Pantene Classic Care Shampoo) is applied down each switch, and then lathered for 30 s by hand before rinsing for 60 s under the shower. The hair is again removed from the shower, and has a further 0.2 g of shampoo applied, and lathered for 30 s before finally rinsing under the shower for 60 s. Hair switches are then left to dry in a controlled temperature cabinet set at 30° C. This washing protocol comprising two shampoo applications and one drying step is defined as a single wash cycle. After this wash cycle is completed, the hair is then defined hereinafter as "virgin" hair and is used hereinafter as a hydrophobic hair substrate.

Chemically Damaged Hair Preparation

Hair switches are chemically damaged using the following two component bleaching formulations:

TABLE 1

| Peroxide base | |
|---|---|
| Ingredients | Wt/Wt % |
| 1. Emulsion base: | |
| Deionized water | 29.78 |
| Cetyl alcohol (1) | 2.24 |
| Stearyl alcohol (2) | 2.24 |
| Ceteareth-25 (3) | 1.50 |
| Phenoxyethanol (4) | 0.11 |
| Sodium benzoate (5) | 0.09 |
| Tetrasodium EDTA (87%) (6) | 0.04 |
| 2. Chelant premix | |
| Deionized water | 35.72 |
| Pentasodium pentetate (40%) (7) | 0.24 |
| Hydroxyethane diphosphonic acid (60%) (8) | 0.16 |
| Phosphoric acid (75%) (9) | 0.08 |
| Sodium stannate (95%) (10) | 0.04 |
| 3. Peroxide mix | |
| Hydrogen peroxide (35%) (11) | 17.15 |
| Deionized water | 10.61 |

TABLE 2

| Carrier base for dye base | |
|---|---|
| Ingredients | Wt/Wt % |
| 1. Acetic acid pre-mix | |
| Deionized water | 46.49 |
| Acetic acid (50%) (12) | 3.91 |
| 2. Emulsion base | |
| Deionized water | 29.78 |
| Cetyl alcohol (1) | 2.24 |
| Stearyl alcohol (2) | 2.24 |
| Ceteareth-25 (3) | 1.50 |
| Phenoxyethanol (4) | 0.11 |
| Sodium benzoate (5) | 0.09 |
| Tetrasodium EDTA (87%) (6) | 0.04 |
| Ammonium hydroxide (13) | 13.60 |

(1): available as Surfac cetyl alcohol from Surfachem, Leeds, UK
(2): available as Surfac stearyl alcohol from Surfachem, Leeds, UK
(3): available as Volpo CS25 from Croda, North Humberside. UK
(4): available as Phenoxyethanol from Nipa-Hardwicke, Wilmington, Delaware
(5): available as Sodium benzoate EP/USP from Haltermann, Cumbria, UK
(6): available as Edeta B powder from BASF, Cheadle, Cheshire, UK
(7): available as Trilon C liquid from BASF, Cheadle, Cheshire, UK
(8): available as Dequest 2010 from Solutia, Newport, South wales
(9): available as Phosphoric acid 750F from Albright & Wilson, West Midlands, UK
(10): available as Sodium stannate, Aldrich
(11): available as Hydrogen peroxide 35% 171/4 from Ellis & Everard, Walsall, UK
(12): available as 50% acetic acid from Hays, Greenwich, London, UK
(13): available as Ammonium Solution BP grade from Brotherton Speciality Products, West Yorkshire, UK These products are made using the following protocols:

Peroxide Base:

The first stage is to make the emulsion base; this is prepared by adding to a vessel deionized water and commencing agitation, and then heating to 82° C. Then tetrasodium EDTA and sodium benzoate are added and dissolved, followed by addition of ceteareth25, cetyl alcohol and stearyl alcohol. During the addition process the temperature is maintained above 80° C., finally phenoxyethanol is added, the mixture is then homogenized for 30 min. The emulsion structure is obtained by cooling whilst still high shear mixing the product down below 50° C. The emulsion base is then left to thicken for 60 min.

The chelants are added to the deionizer water with mixing to form the chelant premix. This is then added with stiffing to the pre-made emulsion base. Adding the peroxide mix water followed by hydrogen peroxide to the emulsion base/chelant premix and stiffing until homogeneous makes the completed peroxide base.

Carrier Base for Dyes

The carrier base for dyes is prepared by adding water to a vessel and commencing agitation, followed by the addition of acetic acid, then by the emulsion base (see emulsion base preparation described hereinbefore for the peroxide base). When fully mixed, ammonium hydroxide is added to the mixture and the stirring continued until the product is homogenous.

To use this bleaching system, equal weights of the two components, the peroxide base and carrier base for dyes are mixed together thoroughly. To each dry untreated hair switch, 4 g of this bleaching system is then applied, and thoroughly worked into the hair, using the fingers, to ensure even, complete, coverage. The hair switch is then wrapped in cling film and incubated in an oven at 30° C. for 30 minutes, after which the product is rinsed for 2 minutes (in a sink fitted with a shower attachment set with a flow rate of 6±1 L min$^{-1}$ and a temperature of 37±2° C.). with finger agitation. Finally the switches are dried using a hot air drier (Babyliss Lightweight Professional model 1015 (1400 W)) for 3 min. The bleached hair switches are then washed in a sink fitted with a shower attachment set with a flow rate of 6±1 L min$^{-1}$ and a temperature of 37±2° C. Switches are initially wetted under the shower attachment for 30 s. The hair is then removed from the water flow and 0.2 g of shampoo (Pantene Clarifying Shampoo) is applied down each switch, and then lathered for 30 s by hand before rinsing for 60 s under the shower. The hair is again removed from the shower, and has a further 0.2 g of shampoo applied, and lathered for 30 s before finally rinsing under the shower for 60 s. Hair switches are then dried using a hot air drier (Babyliss Lightweight Professional model 1015 (1400 W)) for 3 min. This washing protocol comprising two shampoo applications and one drying step is defined as a single wash cycle. This washing method is then repeated again through another complete wash cycle. The dry hair switches are then bleached again according to the method outlined above and subsequently washed again through two complete wash cycles. This hair is hereinafter defined as "damaged" hair and is hereafter used a hydrophilic hair substrate.

Hair Treatment

The functionalized silicone under investigation for deposition and deposition evenness is prepared for assessment using the following method. 28.8 g of the peroxide base, described hereinbefore for use in the preparation of the damaged hair substrate, is weighed into a 100 ml glass beaker; 1.2 g of silicone is then added to the vessel along with a 25 mm magnetic flea and placed on a magnetic stirrer (IKA RCTbasic) and left for 30 min at a stiffing rate of 1000 rpm. This product is then removed from the magnetic stirrer, and 30 g of the carrier base for dyes, described hereinbefore in the preparation of the damaged hair substrate, is then added and thoroughly mixed until homogenous using hand agitation via a plastic spatula. 16 g of the bleaching system containing the silicone under investigation is then applied simultaneously to two virgin and two damaged hair switches (equal to 4 g for each individual switch), held together in the same clamp, and thoroughly worked into the hair, using the fingers, to ensure even, complete, coverage. The hair is then wrapped in cling film and incubated in an oven at 30° C. for 30 minutes after which it is then rinsed for 2 minutes (in a sink fitted with a shower attachment set with a flow rate of 6±1 L min$^{-1}$ and a temperature of 37±2° C.) with finger agitation. The switches are dried using a hot air drier (Babyliss Lightweight Professional model 1015 (1400 W)) for 3 min.

Deposition Measurement

A wavelength dispersive X-Ray Fluoresence spectrometer (Phillips Electronics, PW2404 Sequential "4000W" X-Ray Spectrometer System) is utilized to determine the silicone deposition level on hair. The spectrometer is fitted with a Rhodium tube and includes an InSb crystal to facilitate high sensitivity silicone detection.

Characteristic x-ray photons are produced from the ejection of an inner shell electron of an silicone atom followed by a transition of an electron from a higher energy state to the empty inner shell. X-ray fluorescence of silicone in polydimethylsiloxane (PDMS) is directly proportional to the amount of PDMS deposited on the hair. Any deviations from this relationship that may occur for more functionalized silicones cancels out on calculation of the Deposition Evenness Value (below). A critical component to facilitate the use of XRF technology is the ability to present the sample to the spectrometer in a consistent manner. The hair switch is arranged in a custom-made sample holder, which presents a continuous, flat, aligned hair surface across the exposed sample area (16 mm diameter). The sample is analysed under a helium atmosphere using a Tube voltage of 32 kV and current of 125 mA, with an irradiation/acquisition time of 60 s.

The drift in the analytical signal is regularly monitored and evaluated. The preferred approach employed is to use a known standard that does not need to be prepared each time the drift is assessed. An Ausmon sample is an appropriate monitor sample for many applications, including silicon determinations. A drift correction with the Ausmon sample for silicon is performed at the beginning of each day samples are analyzed. The calculated drift is below 3% between sets of analyses.

Calculation of the amount of silicon on hair in units of ppm from can be made with equation (1).

$$x_2 = (I - b_1)/m_1 \qquad (1)$$

Where $m_1$ and $b_1$ are calculated from a calibration curve constructed from measurements of the XRF signal as a function of the amount of silicone deposited on hair subsequently assayed using atomic absorption on the extracted silicone.

To translate the XRF silicone deposition data obtained as hereinbefore described into a measure of deposition evenness on hair substrates prepared with different levels of chemical damage, it is necessary to generate a deposition evenness value. To generate the deposition evenness value the following equation (2) is employed:

$$\text{Deposition Evenness Value (\%)} = \frac{Dep(1)}{Dep(2)} \times 100 \quad (2)$$

Where Dep(1) equals the XRF deposition value obtained on "damaged" hair (preparation of described hereinbefore), Dep(2) equals the XRF deposition value obtained on "virgin" hair (preparation of described hereinbefore).

Deposition Measurement

Measurement of deposition uses XRF values, as described above for the "Functional Silicone Deposition and Deposition Evenness Determination Method".

To translate the XRF silicone deposition data obtained as hereinbefore described into a measure of silicone durability, it is necessary to generate a silicone durability index value. To generate the silicone durability index value the following equation (3) is employed:

$$\text{Silicone durability index value} = \frac{Dep(12 \text{ cycle})}{Dep(\text{initial})} \quad (3)$$

Where Dep(initial) equals the XRF deposition value obtained on hair after silicone deposition with no washing cycles, Dep(12cycles) equals the XRF deposition value obtained on hair after silicone deposition and subsequent 12 wash cycles.

EXAMPLES AND DATA

Shampoo Compositions

TABLE 3

| Formulation/Component | Typical Shampoo | A | B | C |
|---|---|---|---|---|
| Anionics | | | | |
| Ammonium Lauryl Sulfate | 6 | — | — | — |
| Ammonium Lauryl Ether(3) Sulfate | 10 | — | — | — |
| Sodium Lauryl Sulfate | — | 1.5 | 8.5 | 1.5 |
| Sodium Lauryl Ether (1) Sulfate | — | 16 | 16.5 | 16 |
| C11 Sulfate | — | 6 | — | 6 |
| C10 Sulfate | — | — | 1.5 | — |
| Co-surfactants | | | | |
| Coconut fatty acid MonoEthanolAmide | 1.5 | — | — | — |
| Coco Betaine | — | 2 | — | 1 |
| Cetyl alcohol | 0.9 | — | — | — |
| Cationic Polymer | | | | |
| Guar hydroxypropyltrimonium chloride | — | — | — | 0.1 |
| AM:TRI[1] | 0.5 | 0.1 | 0.1 | — |
| Opacifier | | | | |
| EGDS | 1.5 | 1.5 | 1.5 | 1.5 |
| Benefit Agents | | | | |
| Polydimethylsiloxane[2] | 1.35 | 2.4 | 2.4 | 2.4 |
| Perfume | 0.7 | 1.3 | 1.3 | 1.3 |
| Finishing Agents and water | Balance to 100 | Balance to 100 | Balance to 100 | Balance to 100 |

[1]FORMULA (XI)
[2]Silicone particles about 30 microns

Conditioner Compositions

TABLE 4

| | Typical Conditioner (comparative) | Conditioner A | Conditioner B | Conditioner C |
|---|---|---|---|---|
| Behennial Trimethylammonium chloride (BTMAC) | 2.8 | 2.3 | 3.4 | 2.3 |
| Cetyl Alcohol | 1.9 | 1.5 | 2.2 | 1.5 |
| Stearyl Alcohol | 4.6 | 3.7 | 5.6 | 3.7 |
| Terminal Amino Silicone | 1.5 | 1.5 | 1.5 | 2.5 |
| Ethylene Diamine Tetraacetic Acid (EDTA) | 0.13 | 0.13 | 0.13 | 0.13 |
| Benzyl Alcohol | 0.400 | 0.400 | 0.400 | 0.400 |
| Methylchloroisothiasolinone, Methlisothiazolinone | 0.033 | 0.033 | 0.033 | 0.033 |
| Perfume | 0.35 | 0.35 | 0.35 | 0.35 |
| dl-Pantyl | 0.05 | 0.05 | 0.05 | 0.05 |
| dl-Panthenol | 0.09 | 0.09 | 0.09 | 0.09 |
| Water and minors | Balance to 100 | Balance to 100 | Balance to 100 | Balance to 100 |
| Physical Measure: Yield Point (Y) | 25 | 37 | 52 | 32 |
| X | 9.3 | 7.5 | 11.2 | 7.5 |
| Y ≥ 5.13X − 17.8 | 29.9 | 22.2 | 39.3 | 22.2 |

For Silicone deposition synergy, it is important to demonstrate that we are delivering an equal (or less) amount of silicone to the hair washing/conditioning process, while delivering more silicone to the hair surface.

Example 1

Synergy Between Shampoo A and Conditioner A

TABLE 5

|  | Typical Shampoo PLUS Typical Conditioner | Shampoo A PLUS Typical Conditioner | Typical Shampoo PLUS Conditioner A | Shampoo A PLUS Conditioner A |
| --- | --- | --- | --- | --- |
| Amount of silicone delivered to the wash/rinse (ppm Si) | 2850 | 2700 | 2100 | 1950 |
| Amount of Silicone Extracted from the hair (ppm Si) | 180 | 190 | 245 | 426 |

Example 2

Synergy Between Shampoo B and Conditioner A

TABLE 6

|  | Typical Shampoo PLUS Typical Conditioner | Shampoo B PLUS Typical Conditioner | Typical Shampoo PLUS Conditioner A | Shampoo B PLUS Conditioner A |
| --- | --- | --- | --- | --- |
| Amount of silicone delivered to the wash/rinse (mg Si/dose) | 2850 | 2700 | 2100 | 1950 |
| Amount of Silicone Extracted from the hair (ppm Si) | 180 | 160 | 160 | 229 |

Example 3

Synergy Between Shampoo C and Conditioner A

TABLE 7

|  | Typical Shampoo PLUS Typical Conditioner | Shampoo C PLUS Typical Conditioner | Typical Shampoo PLUS Conditioner A | Shampoo C PLUS Conditioner A |
| --- | --- | --- | --- | --- |
| Amount of silicone delivered to the wash/rinse (mg Si/dose) | 2850 | 2700 | 2100 | 1950 |
| Amount of Silicone Extracted from the hair (ppm Si) | 180 | 190 | 203 | 236 |

Example 4

Synergy Between Shampoo A and Conditioner B

TABLE 8

|  | Typical Shampoo PLUS Typical Conditioner | Shampoo A PLUS Typical Conditioner | Typical Shampoo PLUS Conditioner B | Shampoo A PLUS Conditioner B |
| --- | --- | --- | --- | --- |
| Amount of silicone delivered to the wash/rinse (mg Si/dose) | 2850 | 2700 | 2100 | 1950 |
| Amount of Silicone Extracted from the hair (ppm Si) | 180 | 190 | 237 | 340 |

Example 5

Synergy Between Shampoo A and Conditioner C

TABLE 9

|  | Typical Shampoo PLUS Typical Conditioner | Shampoo A PLUS Typical Conditioner | Typical Shampoo PLUS Conditioner C | Shampoo A PLUS Conditioner C |
| --- | --- | --- | --- | --- |
| Amount of silicone delivered to the wash/rinse (mg Si/dose) | 2850 | 2700 | 2600 | 2450 |

TABLE 9-continued

|  | Typical Shampoo PLUS Typical Conditioner | Shampoo A PLUS Typical Conditioner | Typical Shampoo PLUS Conditioner C | Shampoo A PLUS Conditioner C |
|---|---|---|---|---|
| Amount of Silicone Extracted from the hair (ppm Si) | 180 | 190 | 300 | 400 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multiple product system for keratinic material comprising:
   (1) a hair cleaning composition, for applying from about 0.3 mL to about 0.67 mL per 10 g of hair of the hair cleaning composition, comprising a dermatologically acceptable carrier, and from about 3% to about 40% of at least one surfactant selected from the group consisting of a branched and non-branched versions of decyl and undecyl alkyl sulfates which are either ethoxylated or non-ethoxylated; decyl alcohol modified lauryl sulfate; paraffin sulfonates with chain lengths ranging from $C_{13}$ to $C_{17}$; mixtures of linear and branched-chain alcohol sulfates with carbon chain lengths $C_{12}$ to $C_{17}$ which are ethoxylated or non-ethoxylated; sodium salts of branched, methyl-2-hydroxy-decyl ether sulfates, hydroxyethyl-2-dodecyl ether sulfates, hydroxyethyl-2-decyl ether sulfates; monoethoxylated lauryl alkyl sulfates; and mixtures thereof; and about 0.05 wt % to about 10 wt % of a silicone emulsion; and
   (2) a hair conditioning composition, for applying from about 0.3 mL to about 0.67 mL per 10 g of hair of the hair conditioning composition, comprising:
      (a) a cationic surfactant having the formula (XII):

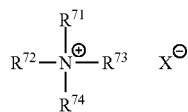

formula (XII)

wherein one of $R^{71}$, $R^{72}$, $R^{73}$ and $R^{74}$ of formula (XII) is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ of formula (XII) are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ of formula (XII) is a salt-forming anion selected from the group consisting of halides such as chloride and bromide, $C_1$-$C_4$ alkyl sulfate, and mixtures thereof;
      (b) a high melting point fatty compound; and
      (c) an aqueous carrier;
   wherein the hair conditioning composition has a yield point of at least 5 Pa, and the yield point meeting the following mathematical expression:

$$Y \geq 5.13X - 17.80$$

wherein Y is yield point of the composition, X is a total amount (percentage by weigh of the composition) of the cationic surfactant and the high melting point fatty compound;
   and wherein the composition is substantially free of thickening polymers;
   wherein upon application of the hair cleaning composition with or in series with the hair conditioning composition to keratinic material, more than about 350 ppm of silicone is deposited on the keratinic material.

2. The multiple product system for keratinic material of claim 1 wherein the at least one surfactant is selected from at least one undecyl sulfate compound selected from the group consisting of: $CH_3$—$(CH_2)_z$—$CHR_2$—$CH_2$—$O(CH_2CHR_3O)_y$—$SO_3M$; where $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation.

3. The multiple product system for keratinic material of claim 1 wherein the high melting point fatty compound is selected from the group consisting of cetyl alcohol, stearyl alcohol and behenyl alcohol.

4. The multiple product system for keratinic material of claim 1 wherein the cationic surfactant is selected from the group consisting of behenyl trimethyl ammonium chloride, methyl sulfate or ethyl sulfate, and stearyl trimethyl ammonium chloride, methyl sulfate and ethyl sulfate.

5. The multiple product system for keratinic material of claim 1 wherein the hair cleaning composition further comprises an additional anionic surfactant.

6. The multiple product system of claim 1 wherein the hair cleaning compositions is substantially free of organic solvent and hydrotrope; and the hair conditioning composition is substantially free of anionic surfactants and anionic polymers.

7. A multiple product system for keratinic material comprising:
   (1) a hair cleaning composition, for applying from about 0.3 mL to about 0.67 mL per 10 g of hair of the hair cleaning composition, comprising a dermatologically acceptable carrier, and from about 3% to about 40% of at least one surfactant selected from the group consisting of: $CH_3-(CH_2)_z-CHR_2-CH_2-O(CH_2CHR_3O)_y-SO_3M$; where $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation; and about 0.05 wt % to about 10 wt % of a silicone emulsion; and (2) a hair conditioning composition, for applying from about 0.3 mL to about 0.67 mL per 10 g of hair of the hair conditioning composition, comprising:
  (a) a cationic surfactant selected from the group consisting of behenyl trimethyl ammonium chloride, methyl sulfate or ethyl sulfate, and stearyl trimethyl ammonium chloride, methyl sulfate and ethyl sulfate;
  (b) a high melting point fatty compound selected from the group consisting of cetyl alcohol, stearyl alcohol and behenyl alcohol; and
  (c) an aqueous carrier;

wherein the hair conditioning composition has a yield point of at least 5 Pa, and the yield point meeting the following mathematical expression:

$$Y \geq 5.13X - 17.80$$

wherein Y is yield point of the composition, X is a total amount (percentage by weigh of the composition) of the cationic surfactant and the high melting point fatty compound;

and wherein the composition is substantially free of thickening polymers;

wherein upon application of the hair cleaning composition with or in series with the hair conditioning composition to keratinic material, more than about 350 ppm of silicone is deposited on the keratinic material; and wherein the hair conditioning composition is substantially free of tertiary amines, tertiary amine salts, and di-long alkyl quaternized ammonium salts.

8. The multiple product system of claim 7 wherein the hair cleaning composition is substantially free of organic solvent and hydrotrope; and the hair conditioning composition is substantially free of anionic surfactants and anionic polymers.

9. The multiple product system for keratinic material of claim 7 wherein the high melting point fatty compound is selected from the group consisting of cetyl alcohol, stearyl alcohol and behenyl alcohol.

10. The multiple product system for keratinic material of claim 7 wherein the cationic surfactant is selected from the group consisting of behenyl trimethyl ammonium chloride, methyl sulfate or ethyl sulfate, and stearyl trimethyl ammonium chloride, methyl sulfate and ethyl sulfate.

11. The multiple product system for keratinic material of claim 7 wherein the hair cleaning composition further comprises an additional anionic surfactant.

* * * * *